(12) United States Patent
Ulbrich et al.

(10) Patent No.: US 8,557,511 B2
(45) Date of Patent: Oct. 15, 2013

(54) METHOD AND APPARATUS FOR INFILTRATING TISSUE SAMPLES WITH PARAFFIN

(75) Inventors: Hermann Ulbrich, Bad Schönborn-Mingolsheim (DE); Michael Rapp, Oftersheim (DE); Marc Konrad, Dossenheim (DE); Holger Metzner, Hassloch (DE); Markus Dobusch, Wiesloch-Baiertal (DE); Eva Goedecke, Plankstadt (DE); Stefan Kuenkel, Karlsruhe (DE); Udo Herrmann, Leimen (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 329 days.

(21) Appl. No.: 12/542,523

(22) Filed: Aug. 17, 2009

(65) Prior Publication Data

US 2010/0055788 A1    Mar. 4, 2010

(30) Foreign Application Priority Data

Aug. 27, 2008  (DE) .......................... 10 2008 039 875

(51) Int. Cl.
*C12M 1/36* (2006.01)
(52) U.S. Cl.
USPC ................ 435/3; 435/40.5; 422/536; 422/50

(58) Field of Classification Search
None
See application file for complete search history.

(56) References Cited

U.S. PATENT DOCUMENTS

| 3,227,130 | A  |   | 1/1966  | Weiskopf |
| 4,001,460 | A  | * | 1/1977  | Kinney et al. ................ 427/2.13 |
| 5,049,510 | A  |   | 9/1991  | Repasi et al. |
| 6,780,380 | B2 | * | 8/2004  | Hunnell et al. ............... 422/536 |
| 2007/0243626 | A1 | | 10/2007 | Windeyer et al. |

FOREIGN PATENT DOCUMENTS

| WO | 96/29866 | 10/1996 |
| WO | 2006/089365 | 8/2006 |

* cited by examiner

*Primary Examiner* — Allison Ford
(74) *Attorney, Agent, or Firm* — Schlee IP International, P.C.; Alexander R. Schlee

(57) ABSTRACT

A method and an apparatus are described for infiltrating tissue samples with carrier material, preferably paraffin. A supply of carrier material is kept ready for use in a supply station. From there, the carrier material can be delivered into at least a first and a second container. In these first and second containers carrier materials of differing degrees of purity are kept ready for use, respectively, for performing various infiltration steps on tissue samples. By means of the described method and apparatus the tissue processor can be operated with as little interruptions as possible and an ease in operation is achieved.

3 Claims, 4 Drawing Sheets

METHOD AND APPARATUS FOR INFILTRATING TISSUE SAMPLES WITH PARAFFIN

CROSS-REFERENCE TO RELATED APPLICATION

This application claims the priority of the German patent application DE 102008039875.6 having a filing date of Aug. 27, 2008. The entire content of this prior German patent application DE 102008039875.6 is herewith incorporated by reference.

BACKGROUND OF THE INVENTION

The invention relates to a method for infiltrating tissue samples with carrier material, said tissue sample being treated in multiple infiltration steps with carrier material of an increasing degree of purity. The invention further relates to an apparatus for carrying out the method.

Biological tissue samples, in particular histological tissue samples, are often required in the fields of human and veterinary medicine, in particular as microscopic prepared specimens for the assessment of cells and their environment. For microscopic inspection, thin sections of the tissue sample must be prepared for assessment under the microscope, in incident or transmitted light, by an expert. The tissue sample must have a certain strength for the production of thin sections, for example using a microtome, so that thin, transparent sections having a thickness on the order of micrometers can be produced using a knife. For this purpose, the tissue sample must first pass through a treatment process in which it is fixed, dehydrated, cleared, and then infiltrated with a carrier material, preferably melted paraffin. These processes are often performed successively in a single unit called a "tissue processor"; this tissue processor contains a closable process chamber called a "retort" that receives the various reagents for carrying out the process steps at a suitable temperature and pressure.

One important process step in this context is infiltration of the tissue sample with the carrier material in order to stabilize and consolidate it. This infiltration process step is preceded by the clearing step, in which alcohol residues still present from the preceding dehydration step are removed. The chemical solution used for this clearing step is xylene or a similar medium. In the subsequent infiltration step, in which the tissue sample is exposed to the carrier material (usually melted paraffin), xylene constituents that still remain are flushed out and taken up by the liquid carrier material, with the result that the carrier material in the retort becomes contaminated. Constituents from the tissue sample itself can also contaminate the carrier material. It is therefore necessary to divide the overall infiltration process into multiple individual steps in which the tissue sample is exposed successively to different carrier materials of increasing purity. If the infiltration process is divided into three process steps, for example, the tissue sample is then first treated with a first carrier material that can have a relatively high level of contamination (e.g. with xylene). This is followed by a second infiltration step using a second carrier material that has a higher degree of purity than the first carrier material. Lastly, the tissue sample is exposed to a third carrier material that has the highest degree of purity. In this fashion the tissue sample is completely infiltrated, in a graduated process in which the carrier material for treatment is of increasing purity, with carrier material that has sufficient quality to produce a good thin section in a microtome, and for a microscopic prepared specimen.

The use of multiple liquid carrier materials having different degrees of purity requires that these carrier materials be kept available in containers in a liquid state. If one of the carrier materials is too highly contaminated, this usually affects the aforesaid first carrier material, and it must be replaced with a carrier material having an improved degree of purity. In the case of paraffin, it must be melted from its solid state as stored, typically in the form of paraffin pellets or flakes, until the quantity necessary for replacement is available. Because the carrier material often contains certain chemical additives that are volatile, the melting operation must occur relatively slowly; in practice, this can take several hours. If melting is accomplished in a container inside the tissue processor, said tissue processor is then not operational for that period of time. If the melting process is accomplished outside the tissue processor, this has the disadvantage that the handling of hot, liquid carrier material is relatively difficult for operators; the filling operation into a container inside the tissue process is especially problematic. The bulk volume of paraffin pellets or flakes is considerably greater than the liquid volume of the melted paraffin for the same unit weight. As the paraffin melts it is therefore necessary to top up the melting container several times with solid paraffin in order to obtain the desired volume of molten, liquid paraffin in a compact container.

WO 2006/089365 A1 discloses a method and an apparatus for tissue treatment in which liquid paraffin is used for infiltrating tissue samples. The solid starting material used is blocks of paraffin that are melted in special containers inside a tissue processor. The use of paraffin in block form has the advantage that the desired quantity of liquid paraffin can be estimated relatively accurately based on the size of the block shape.

SUMMARY OF THE INVENTION

It is an object of the invention to describe a method and an apparatus for infiltrating tissue samples with carrier material, in which the method and the tissue processor can be operated in as uninterrupted a fashion as possible, and in which simplified operation is achieved.

This object is achieved by a method for infiltrating tissue samples with carrier material, comprising the method steps of: placing the tissue sample in a retort; treating the tissue sample in a first treatment step in the retort with a first carrier material having a first degree of purity; treating the tissue sample in a second treatment step performed subsequently to the first treatment step with at least one second similar carrier material of a second degree of purity that is higher than the first degree of purity; replacing the respective carrier material, when a predetermined degree of contamination is exceeded, by a less-contaminated carrier material; keeping a supply of uncontaminated carrier material ready for use in a melted state; using the second carrier material as a first carrier material when the first carrier material or the second carrier material reaches a predetermined degree of contamination; and using uncontaminated carrier material from the supply as a second carrier material. Accordingly, the apparatus for performing the aforementioned method of infiltrating tissue samples with carrier material comprises a retort for receiving tissue samples, a supply station for receiving uncontaminated carrier material, in particular paraffin, a first container for receiving a first carrier material in a liquid state, at least one second container for receiving a second carrier material in a liquid state, and a system of conduits that interconnects the supply station, the retort, and the first and second containers.

According to the invention, in a process for infiltrating tissue samples with carrier material, in particular paraffin or wax, the tissue sample in the retort is treated firstly with a first carrier material having a reduced degree of purity, and then at least with one second similar carrier material having an elevated degree of purity. A supply of uncontaminated carrier material is kept on hand in a melted state, in particular inside the tissue processor. When the first carrier material having a reduced degree of purity has reached a predetermined degree of contamination and must be replaced, a resequencing is performed in which the second carrier material is used as a first carrier material; the uncontaminated carrier material from the supply is used as a second carrier material. The contaminated carrier material, in particular the formerly first carrier material, is removed from the tissue processor. Subsequent tissue samples are therefore treated with a first carrier material that was previously used as a second carrier material. In the next process step the tissue sample is then treated with the uncontaminated carrier material from the supply, i.e. it is used as a new second carrier material.

It may also happen, in the case of an operating malfunction, that the second carrier material has too high a degree of contamination and no longer possesses the requisite quality that would be necessary for the second carrier material. In this case as well, a resequencing occurs in which the second carrier material, if it is still suitable for the purpose based on the degree of contamination, is used as a first carrier material; the uncontaminated carrier material from the supply is used as a new second carrier material.

For the case in which three infiltration steps are provided for the treatment of tissue samples, and three carrier materials having different degrees of purity are used, then once again a resequencing occurs in which, in most cases, the first carrier material is removed and the second carrier material is used in its place. The formerly third carrier material is used as a new second carrier material. The uncontaminated carrier material from the supply is used as a new third carrier material.

The procedure is analogous when four or more infiltration steps are utilized. One carrier material is removed, and the uncontaminated carrier material from the supply is used for the last infiltration step. The above-described resequencing of the carrier materials is performed for the other infiltration steps.

The advantage of making available a supply of uncontaminated carrier material in a melted state is that this supply can already be melted while the carrier materials being used in the infiltration process still have a sufficiently low degree of contamination to ensure proper quality in terms of tissue sample treatment. When the degree of contamination for a carrier material then becomes too high, carrier material for the infiltration process can then be added immediately, without major interruption, from the supply that has been made ready. The handling of hot, liquid carrier material is thus eliminated. A period of interruption in the infiltration process is also avoided. The melting operation for the carrier material of the supply can occur slowly and gently, since sufficient time for it is generally available. Thanks to the resequencing described above, only a small portion of the total quantity of similar carrier material being used needs to be removed, with the result that carrier material consumption is reduced.

The method and the apparatus can be configured in such a way that the supply of carrier material is kept on hand in a supply station inside a tissue processor. This supply station melts solid carrier material with the aid of a controllable heating apparatus. This solid carrier material can be present, for example, in the form of pellets, tablets, flakes, or blocks. The volume of the supply station can preferably be dimensioned so that it receives solid carrier material in a single filling operation, and the melted volume of carrier material in the supply station is sufficient to fill at least one of the containers from which the first carrier material, the second carrier material, and if applicable the third carrier material are delivered into the retort and conveyed back therefrom.

According to a further aspect of the invention, an apparatus for carrying out the invention is described.

BRIEF DESCRIPTION OF THE DRAWINGS

Exemplifying embodiments of the invention are explained below with reference to the appended drawings, in which.

DETAILED DESCRIPTION OF THE DRAWINGS

Figure 1:
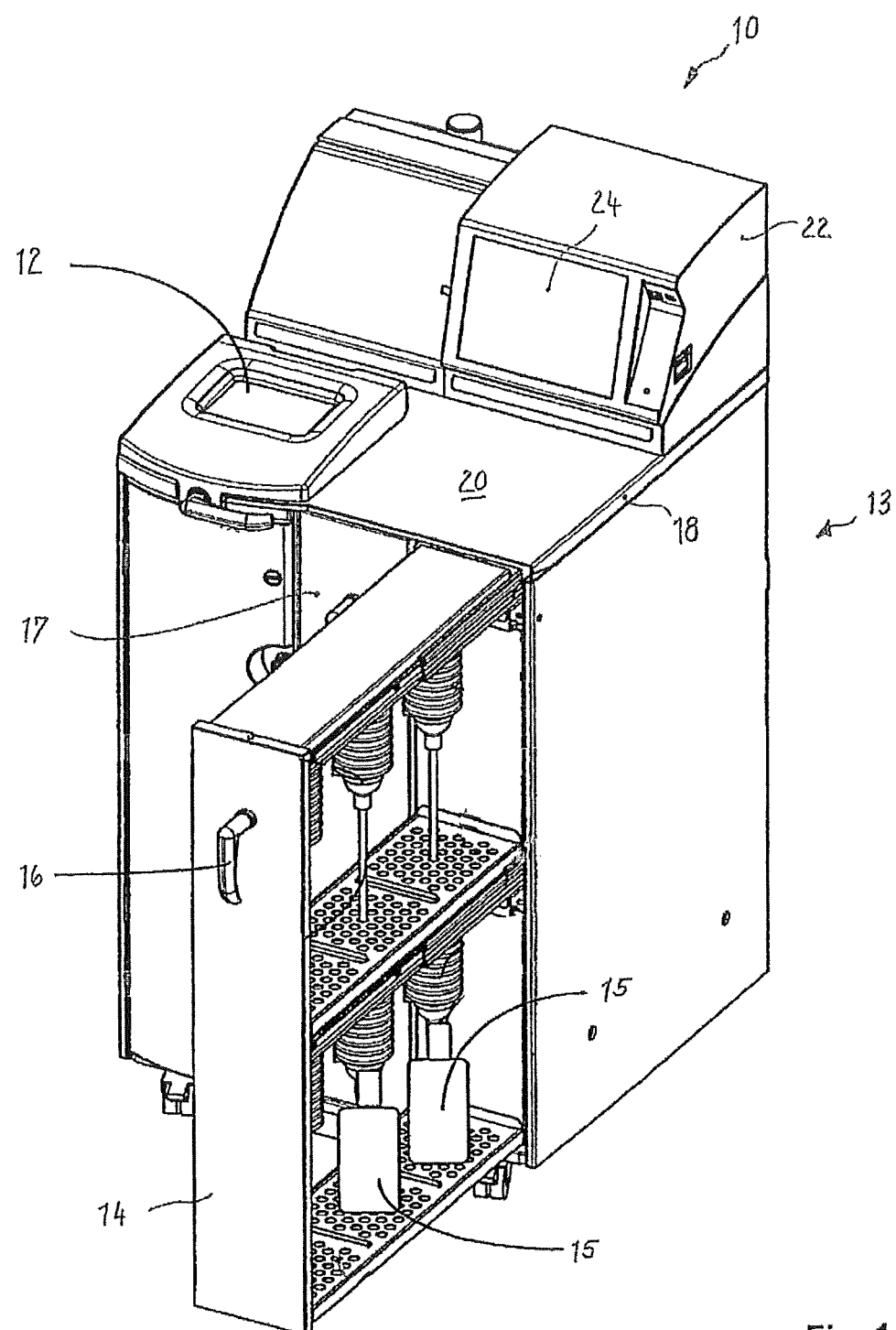
FIG. 1 shows a tissue processor.

FIG. 1 schematically shows a tissue processor 10 with which the method according to the present invention can be carried out. Tissue processor 10 contains a retort 12 for processing tissue samples using various reagents. In said retort 12, the tissue samples pass through a fixing process in which formalin is typically used. A dehydration process is then accomplished, using alcohol solutions of various degrees of purity. In a subsequent clearing process, alcohol residues are removed from the tissue samples, and the tissue samples are prepared for the uptake of carrier material. Xylene or a similar medium is often used in this clearing process. Paraffin or wax of various compositions is preferably suitable as a carrier material.

Tissue processor 10 encompasses a cabinet 13 having drawers. One drawer 14 serves for the reception of reagents 15 (only two of many are shown) that are necessary so that the fixing process, the dehydration process, and/or the clearing process can be carried out. Drawer 14 has a handle 16 for actuation. A further drawer 17 (only partially shown) contains components for the infiltration process described below.

A work area 20 is provided on a desktop 18. Also arranged on desktop 18 is a control device 22 having a screen 24. Control device 22 controls the treatment processes for the tissue samples with the assistance of a computer.

Figure 2:
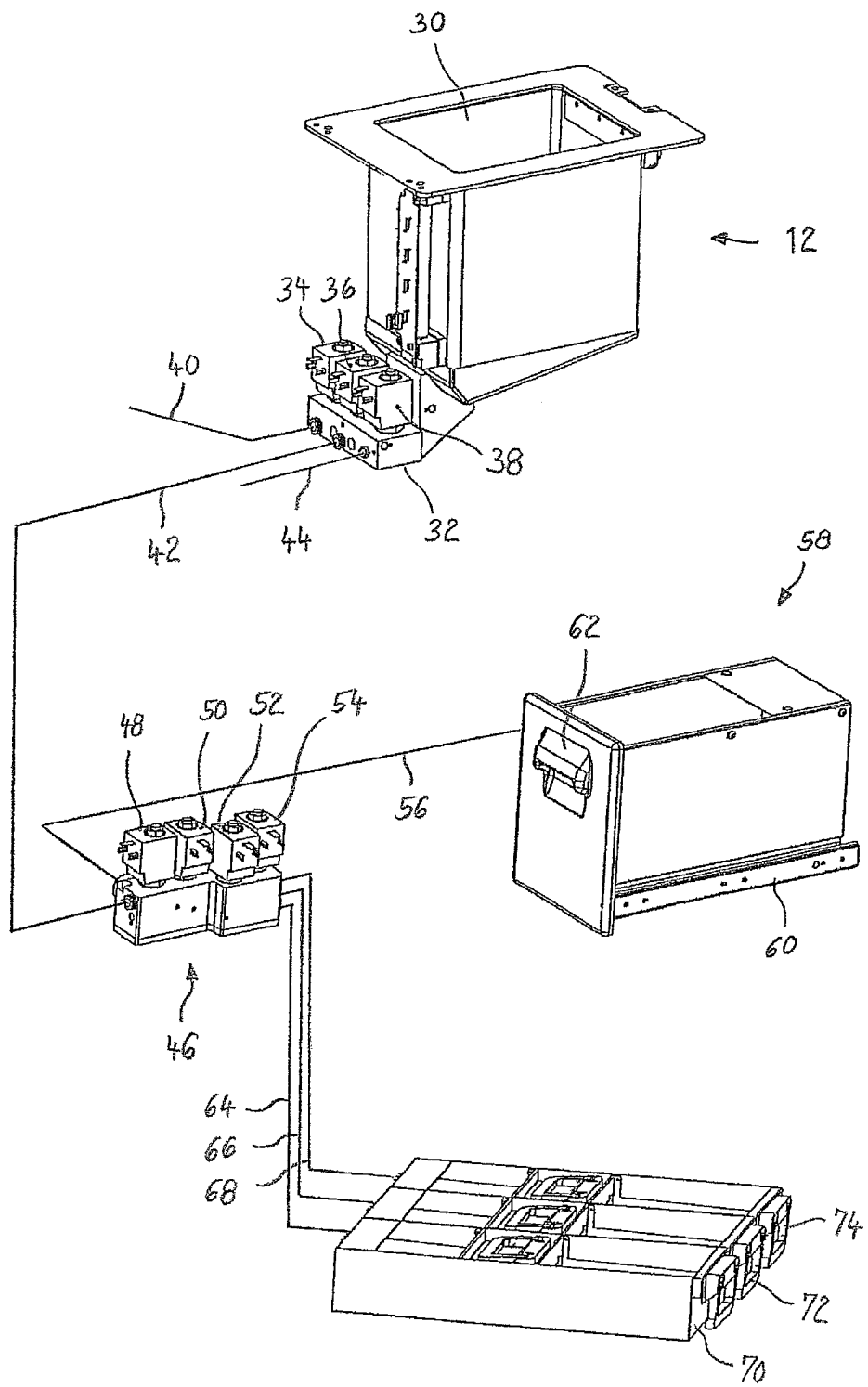
FIG. 2 shows various components of a tissue processor relevant to the infiltration of tissue samples with paraffin.

FIG. 2 shows important components for carrying out the method for infiltrating tissue samples with carrier material, in particular paraffin or wax. Identical parts in the various Figures are labeled identically.

Retort 12 is embodied as a sealable chamber having an opening 30 that can be closed off. Inside retort 12, a variety of reagents, in particular the paraffin that is important for the infiltration process, can be acted upon by pressure, vacuum, and temperature. The interior of retort 12 is connected via a valve arrangement 32 to conduits 40, 42, 44 via electrically controllable valves 34, 36, 38 respectively. The purpose of conduit 40 can be that, under the control of valve 34, liquid paraffin that is contaminated can be removed.

Conduit 42 is connected via valve 36 to the contents of retort 12. Under the control of valve 36, liquid paraffin is delivered in and back out through conduit 42. A further conduit 44 serves for connection to further reagents for the fixing process, the dehydration process, and/or the clearing process, although this is not further described here.

Conduit 42 is connected to a distributor 46 that distributes liquid paraffin under the control of valves 48, 50, 52, 54. Connected to distributor 46 is conduit 56, which connects the distributor to a supply station 58 for paraffin. Supply station 58 is embodied as a drawer, and contains extension rails 60 and a handle 62.

Also connected to distributor 46 are three conduits 64, 66, 68 that connect it to a first container 70, a second container 72, and a third container 74. These containers 70, 72, 74 contain liquid paraffin with an increasing degree of purity. Containers 70, 72, 74 are also configured as drawers, and can be pulled out of the chamber of tissue processor 12 and then removed.

All the conduits 40, 42, 56, 64, 66, 68 are heated, as are valve arrangement 32 and distributor 46, in order to ensure that the paraffin is always kept in a liquid state, e.g. at 65° C., and does not solidify during operation. The same is also true of retort 12 and its parts, and of supply station 58 and containers 70, 72, 74. The corresponding heating elements have been omitted from the Figure for reasons of clarity.

Supply station 58 has a considerably larger volume than the respective containers 70, 72, 74. It also serves to melt paraffin that is present in the solid state as paraffin pellets or flakes. The bulk volume of paraffin pellets or flakes is considerably larger than the liquid volume of the melted paraffin for the same weight. The enlarged volume of supply station 58 thus allows a sufficiently large bulk volume of solid paraffin to be introduced, with no need to add more solid paraffin for a sufficient liquid supply. This facilitates the handling of solid paraffin. In addition, the liquid volume of supply station 58 is sufficiently large that containers 70, 72, 74 can be provided with uncontaminated paraffin for a relatively long operating time, for example even for automatic operation during the night, when operators do not need to be present.

Figure 3:
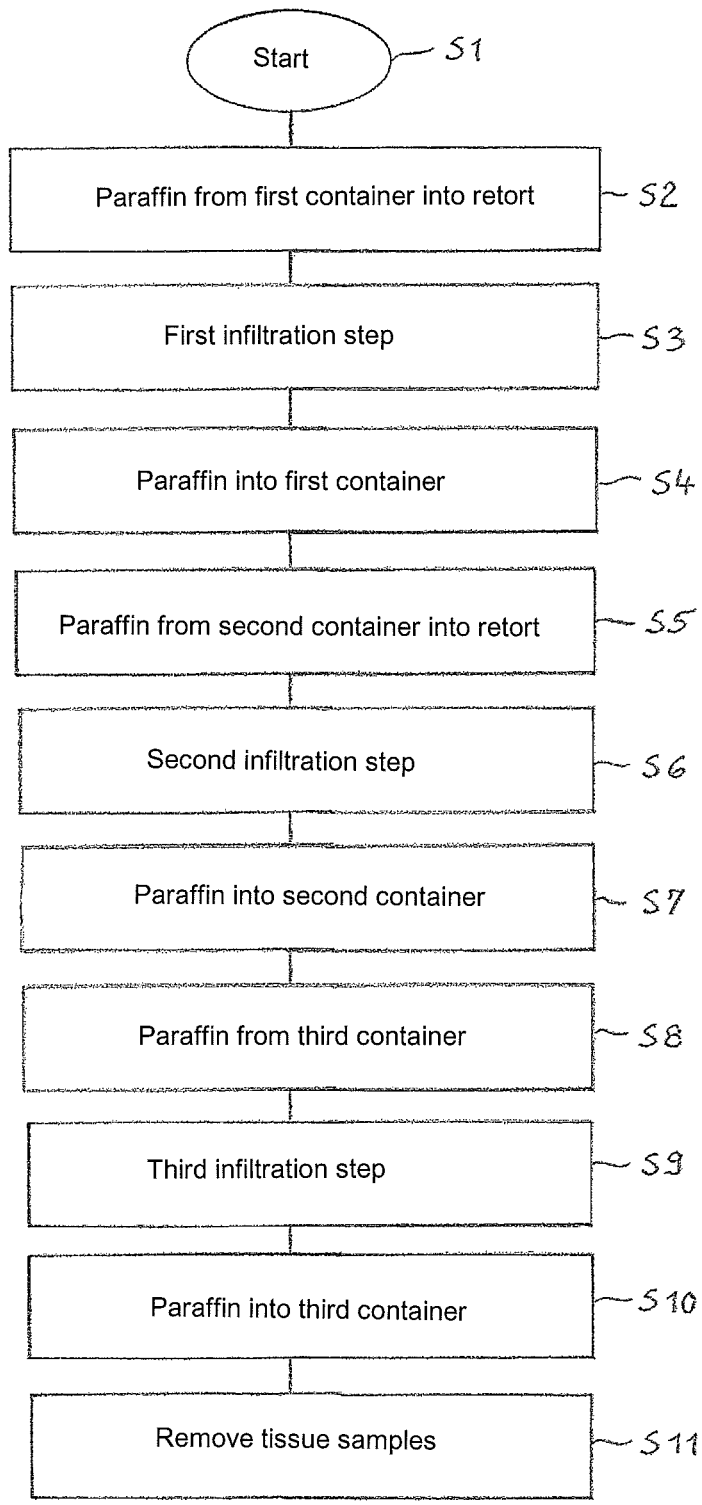
FIG. 3 is a flow chart showing the various process steps for infiltration with paraffin.

FIG. 3 indicates the sequence of the infiltration process in three stages, with reference to a flow chart. After starting (step S1), liquid paraffin is delivered out of first container 70 into retort 12. For this purpose, vacuum is applied to the closed chamber of retort 12 so that paraffin is delivered into retort 12 through conduit 64, distributor 46, conduit 42, and valve 36 in sufficient quantity to surround the tissue samples up to a specific fill height that is ascertained with the aid of a sensor (step S2). To assist the infiltration process, retort 12 can be acted upon by pressure and the liquid paraffin can be recirculated, thus infiltrating the tissue samples (step S3). After completion of the first stage of the infiltration process, the paraffin is delivered back out of the retort in the opposite direction into first container 70, retort 12 preferably being acted upon by compressed air (step S4). Alternatively, it may also be sufficient if, with a suitable configuration, the liquid paraffin flows back into first container 70 under its own weight (step S4).

Because the tissue samples still, in this first infiltration step, contain clearing medium (preferably xylene) from the preceding clearing step, the paraffin inevitably becomes contaminated to a certain degree with that clearing medium. In the subsequent second infiltration step, firstly paraffin is delivered out of second container 72 into retort 12 (step S5). This paraffin of second container 72 has a higher degree of purity than the paraffin of first container 70. The tissue samples are once again treated in retort 12 using the paraffin from the second container (step S6). After a predetermined treatment time, the paraffin is delivered back into second container 72 (step S7).

A third infiltration step then occurs using paraffin of an even higher degree of purity than the paraffin present in second container 72. In step S8, paraffin from third container 74 is delivered into retort 12 and, in step S9, the tissue samples are treated with that paraffin for a predetermined treatment time. In step S10, the paraffin present in retort 12 is then delivered back into third container 74.

The infiltration process for the tissue samples is now complete. The tissue samples are removed from retort 12 and cool off (step S11).

Figure 4:
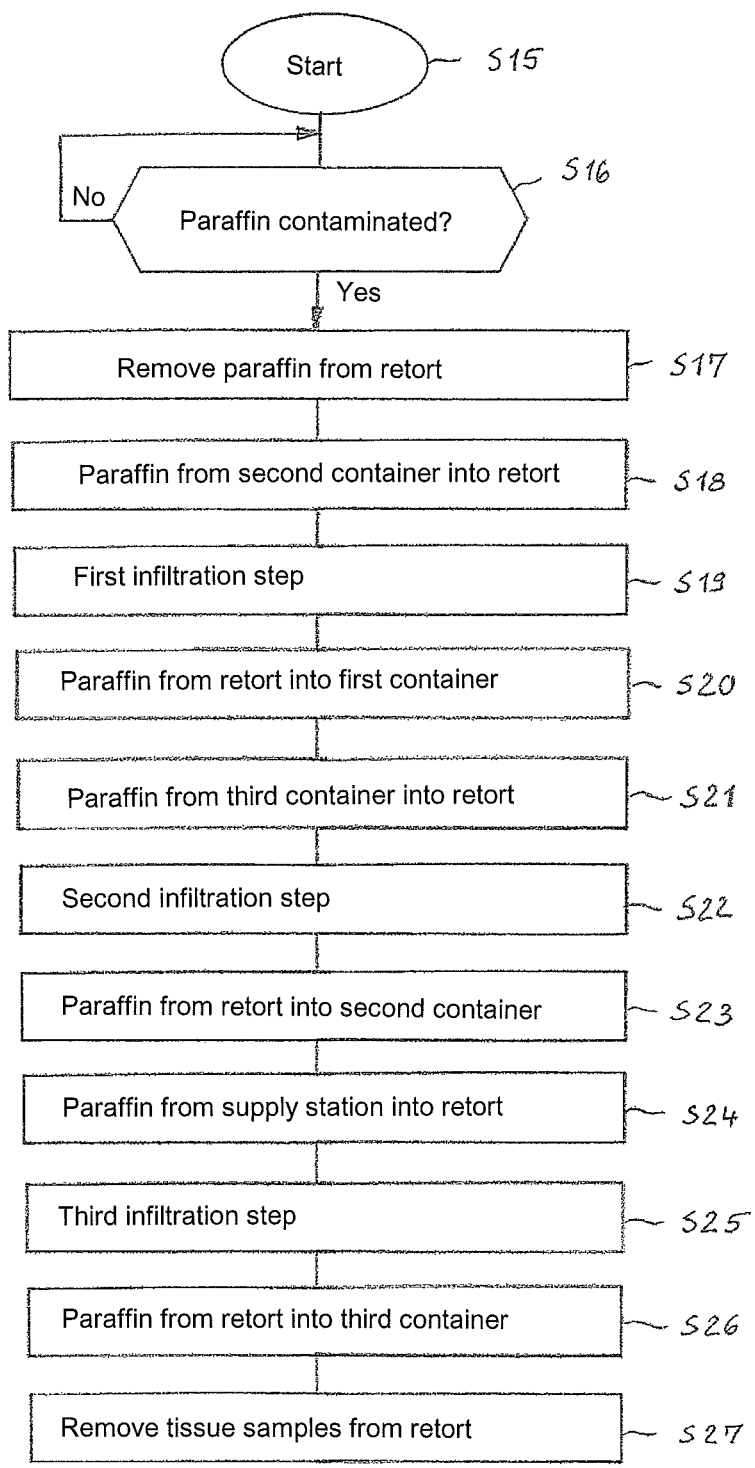
FIG. 4 is a flow chart with resequencing of the various paraffin containers.

FIG. 4 shows, in a flow chart, the process sequence for the case in which contaminated paraffin needs to be replaced. After starting (step S15), step S16 queries whether the paraffin from first container 70 in retort 12 is contaminated. This query step can be accomplished before an infiltration treatment of the tissue samples in retort 12, or when the tissue samples have already gone through the first infiltration step. The contamination is typically ascertained on the basis of empirical values, i.e., it is known from experience that after a certain number of first infiltration steps, the degree of contamination is so high that in order to maintain good infiltration quality, it is now necessary not to use that paraffin further, and to replace it with a paraffin of better purity. Another method is to ascertain, with the aid of a sensor, whether or not a predetermined degree of contamination has or has not been exceeded. If the degree of contamination is still sufficiently low, execution then branches back in accordance with query step S16, and method steps S3 to S11 proceed in accordance with FIG. 3. If the degree of contamination is exceeded, execution then branches to the next step S17.

In step S17, the contaminated paraffin is removed from retort 12, for example via conduit 40, delivered into a storage container, and processed and purified if applicable. In the next step S18, for the case in which the tissue samples have not yet been treated in accordance with the first infiltration step, paraffin is delivered out of second container 72 into retort 12. In step S19, treatment of the tissue samples in accordance with the first infiltration step then occurs (step S19).

The paraffin deriving from second container 72 is then not transported back into second container 72, however, but instead is delivered through valve 36, conduit 42, distributor 46, and conduit 64 into first container 70 (step S20). A resequencing therefore takes place, such that, what is used for the tissue samples for future first infiltration steps is paraffin from first container 70, which was previously used as paraffin for the second infiltration step.

After completion of the first infiltration step, in step S21 paraffin is delivered from third container 74 into retort 12, and the second infiltration step is accomplished for the tissue samples present therein (steps S21 and S22). Paraffin deriving from third container 74 is then delivered through valve 36, conduit 42, distributor 46, and conduit 66 into second container 72, and used in the future for the second infiltration step (step S23).

For the third infiltration step, firstly uncontaminated paraffin is delivered from supply station 58 through conduit 56, distributor 46, conduit 42, and valve 36 into retort 12 (step S24), and the tissue samples are correspondingly treated. After the preset treatment time, the paraffin is delivered through valve 36, conduit 42, distributor 46, and conduit 68 into third container 74 (step S26). This container 74 then contains, in an almost pure state, the paraffin deriving from supply station 58, which is used in future for the third infiltration stage for the tissue samples. In step S27, the treated tissue samples are removed from retort 12 and cool off.

If no tissue samples are contained in retort 12, it can be used as a temporary container for liquid paraffin. Paraffin can be delivered out of one of containers 70, 72, 74, or out of supply station 58, into retort 12. From there the paraffin can be distributed by appropriately applying control to valves 34, 36, 48, 50, 52, 54, in which context, in particular, the above-described resequencing of paraffin containers 70, 72, 74 can be performed and/or damaged paraffin can be removed.

The exemplifying embodiments according to FIGS. 1 to 4 were described using paraffin as a carrier material for infiltrating tissue samples. A different liquid carrier material, which is kept on hand in containers 70, 72, 74 and in supply station 58 at different degrees of purity, can also be used in the same way.

The various method steps are controlled in largely automatic fashion with the aid of control device 22 (cf. FIG. 1). The method steps that are carried out are displayed on screen 24 in a block diagram. An operator can also intervene manually in the process sequence and, for example, apply control to tissue processor 10 in such a way that liquid paraffin can be removed from the various containers 70, 72, 74 or from supply station 58, using retort 12 as a temporary container. It is likewise possible to transfer the contents of the various containers 70, 72, 74 and of supply station 58.

| List of component parts | |
|---|---|
| 10 | Tissue processor |
| 12 | Retort |
| 13 | Cabinet |
| 14 | Drawer |
| 15 | Reagents |
| 16 | Handle |
| 17 | Drawer |
| 18 | Desktop |
| 20 | Work area |
| 22 | Control device |
| 24 | Screen |
| 30 | Opening |
| 32 | Valve arrangement |
| 34, 36, 38 | Valves |
| 40, 42, 44 | Conduits |
| 46 | Distributor |
| 48, 50, 52, 54 | Valves |
| 56 | Conduit |
| 58 | Supply station |
| 60 | Extension rails |
| 62 | Handle |
| 64, 66, 68 | Conduits |
| 70 | First container |
| 72 | Second container |
| 74 | Third container |
| S1 to S27 | Method steps |

What is claimed is:

1. A method for infiltrating tissue samples with carrier material, comprising the method steps of:
   (a) opening a retort and placing at least one first tissue sample in the retort;
   (b) closing the retort and applying a vacuum to the retort for filling the retort from a first container via a distributor with a first carrier material having a first degree of purity;
   (c) treating the at least one first tissue sample in a first treatment step in the retort with the first carrier material having a first degree of purity;
   (d) determining whether the first carrier material has reached a predetermined degree of contamination;
   (e) applying a pressure to the retort for removing the first carrier material from the retort into the first container;
   (f) applying a vacuum to the retort for filling the retort from a second container via the distributor with a second carrier material that is similar to the first carrier material and has a second degree of purity that is higher than the first degree of purity;
   (g) treating the at least one first tissue sample in a second treatment step performed subsequently to the first treatment step with the second carrier material;
   (h) applying a pressure to the retort for removing the second carrier material via the distributor from the retort into the second container;
   (i) applying a vacuum to the retort for filling the retort from a third container via the distributor with a third carrier material that is similar to the first carrier material and has a third degree of purity that is higher than the second degree of purity;
   (j) treating the at least one first tissue sample in a third treatment step performed subsequently to the second treatment step with the third carrier material;
   (k) applying a pressure to the retort for removing the third carrier material via the distributor from the retort into the third container;
   (l) opening the retort and removing the at least one first tissue sample from the retort;
   (m) using the retort with no samples contained in the retort as a temporary container for distributing the liquid carrier material to containers in the subsequent steps (n)-(t) as follows:
   (n) closing the retort and applying a vacuum to the retort for filling the retort via the distributor from the first container with the first carrier material;
   (o) applying a pressure to the retort for removing the first carrier material from the retort and discard it directly through a conduit when it was determined in step (d) that the first carrier material has reached a predetermined degree of contamination;
   (p) keeping a supply of uncontaminated fourth carrier material ready in a supply station for use in a melted state;
   (q) applying a vacuum to the retort for filling the retort via the distributor from the supply with the uncontaminated fourth carrier material;
   (r) applying a pressure to the retort for removing the uncontaminated fourth carrier material via the distributor from the retort into the first container;
   (s) resequencing the carrier materials for the further treatment of tissue samples by using the formerly second carrier material in future as a first carrier material, using the formerly third carrier material in future as a second carrier material, and using the fourth uncontaminated carrier material in future as the third carrier material; and
   (t) (repeating steps (a)-(l) for treatment of at least one second tissue sample.

2. The method according to claim 1, further comprising the method step of using at least one of paraffin, wax, and an infiltration substance that consolidates the tissue sample after infiltration as a carrier material.

3. The method according to claim 1, further comprising the method step of providing the carrier material in solid form as at least one of pellets, tablets and flakes.

* * * * *